US009457348B2

(12) United States Patent
Clavaguera et al.

(10) Patent No.: US 9,457,348 B2
(45) Date of Patent: Oct. 4, 2016

(54) DEVICE FOR SAMPLING AND TRANSPORTING NANO-OBJECTS CONTAINED IN AEROSOLS FOR THE ANALYSIS THEREOF

(71) Applicants: COMMISSARIAT A L'ENERGIE ATOMIQUE ET AUX ENE ALT, Paris (FR); NANOBADGE, Peronnas (FR)

(72) Inventors: Simon Clavaguera, Alenya (FR); Eric Decolin, Montbonnot Saint Martin (FR); Guillaume Hebert, La Tronche (FR); Jean-Loup Rechatin, Corenc (FR); Francois Tardif, Lans en Vercors (FR)

(73) Assignees: Commissariat à l'énergie atomique et aux énergies alternatives, Paris (FR); NANOBADGE, Peronnas (FR)

( * ) Notice: Subject to any disclaimer, the term of this patent is extended or adjusted under 35 U.S.C. 154(b) by 29 days.

(21) Appl. No.: 14/349,249

(22) PCT Filed: Oct. 5, 2012

(86) PCT No.: PCT/EP2012/069774
§ 371 (c)(1),
(2) Date: Apr. 2, 2014

(87) PCT Pub. No.: WO2013/050561
PCT Pub. Date: Apr. 11, 2013

(65) Prior Publication Data
US 2014/0286836 A1    Sep. 25, 2014

(30) Foreign Application Priority Data
Oct. 5, 2011    (FR) ...................................... 11 58997

(51) Int. Cl.
*G01N 37/00*    (2006.01)
*G01N 1/00*    (2006.01)
(Continued)

(52) U.S. Cl.
CPC ........... *B01L 3/5023* (2013.01); *G01N 1/2205* (2013.01); *G01N 2001/2276* (2013.01); *G01N 2001/2288* (2013.01)

(58) Field of Classification Search
CPC .............. B01L 3/5023; G01N 1/2205; G01N 2001/2276; G01N 2001/2288; Y10T 16/56; Y10T 15/568; Y10T 16/577; Y10T 16/585; Y10T 16/593; Y10T 16/595; B01D 2201/40; B01D 2201/4007; B01D 2201/4015; B01D 2201/4023; B01D 2201/403; B01D 2201/4038; B01D 2201/4046; B01D 2201/4053; B01D 2201/4061; B01D 2201/4069; B01D 2201/4076; B01D 2201/4084; B01D 2201/4092
See application file for complete search history.

(56) References Cited

U.S. PATENT DOCUMENTS 3,966,439 A    6/1976    Vennos
4,961,916 A    10/1990   Lesage et al.
(Continued)

FOREIGN PATENT DOCUMENTS

CN    2306014 Y    2/1999
CN    101261202 A    9/2008
(Continued)

OTHER PUBLICATIONS

Furuuchi, Masami, et al. "Development and performance evaluation of air sampler with inertial filter for nanoparticle sampling." Aerosol Air Qual. Res 10 (2010): 185-192.*
(Continued)

*Primary Examiner* — Lyle Alexander
*Assistant Examiner* — Robert Eom
(74) *Attorney, Agent, or Firm* — Oblon, McClelland, Maier & Neustadt, L.L.P.

(57) ABSTRACT

A device for sampling and transporting nano-objects for analysis thereof. A cassette portion of the device includes two parts with mutual assembly mechanisms between them including a clipping mechanism configured not to be accessible from outside in assembled position of the parts. Therefore, any inopportune opening of the cassette and thus extraction of the sampling filter accommodated in the cassette somewhere else than the place intended for the analysis are avoided.

18 Claims, 3 Drawing Sheets

(51) Int. Cl.
B01D 25/00 (2006.01)
B01L 3/00 (2006.01)
G01N 1/22 (2006.01)

(56) References Cited

U.S. PATENT DOCUMENTS

| | | | |
|---|---|---|---|
| 4,965,955 A * | 10/1990 | Campbell | A01K 63/02 |
| | | | 119/201 |
| 5,205,155 A | 4/1993 | Cooper | |
| 7,651,543 B1 | 1/2010 | Marple et al. | |
| 2004/0043443 A1 | 3/2004 | Lejeune | |
| 2007/0240492 A1* | 10/2007 | DiLeo et al. | 73/38 |
| 2008/0196514 A1 | 8/2008 | Kenny | |
| 2009/0272202 A1 | 11/2009 | Uang et al. | |
| 2012/0164399 A1 | 6/2012 | Rey et al. | |

FOREIGN PATENT DOCUMENTS

| | | | |
|---|---|---|---|
| CN | 102162527 A | 8/2011 | |
| DE | 3126850 A1 * | 3/1982 | B01D 13/04 |
| DE | 3526495 A1 | 2/1986 | |
| JP | 2008-180553 A | 8/2008 | |
| JP | 2011-080982 A | 4/2011 | |

OTHER PUBLICATIONS

Furuuchi, Masami, et al. "Development of a personal sampler for evaluating exposure to ultrafine particles." Aerosol Air Qual. Res 10.1 (2010): 30-37.*
Combined Office Action and Search Report issued May 25, 2015 in Chinese Patent Application No. 201280057259.9 ( with English language translation and English translation).
International Search Report issued Dec. 12, 2012 date in PCT/EP12/69774 filed Oct. 5, 2012.
French Search Report issued Apr. 10, 2012 in French Application No. 11 58997 filed Oct. 5, 2011.
U.S. Appl. No. 13/376,033, filed Mar. 19, 2012, Rey, et al.
U.S. Appl. No. 14/349,249, filed Apr. 2, 2014, Clavaguera, et al.
Japanese Office Action issued Jul. 28, 2016, in Japanese Patent Application No. 2014-533927 (English translation provided).

* cited by examiner

FIG.5

DEVICE FOR SAMPLING AND TRANSPORTING NANO-OBJECTS CONTAINED IN AEROSOLS FOR THE ANALYSIS THEREOF

TECHNICAL FIELD

The invention relates to a device for sampling and transporting nano-objects contained in aerosols for the analysis thereof.

More particularly, the invention is applicable to sampling and transporting nanoparticles or nano-objects contained in aerosols.

By nano-objects, it is meant objects at least one unit size of which is lower than about 100 nm.

By nanoparticle, it is meant particles generally (but not only) spherical which unit average diameter is lower than about 100 nm, in accordance with ISO TS/27687 standard.

The invention is also applicable to sampling and transporting micrometric size particles contained in aerosols.

PRIOR ART

The rapid growth of nanotechnologies has made essential the implementation of works on the health and environmental impacts of these new materials in order to ensure optimum safety conditions, in particular for operators (workers) in a station for making nano-objects or developing nanomaterials.

For a few years, nanometric size particles have been intensively researched and their use has started to spread in various fields such as health, microelectronics, energy technologies or consumer products such as paints and cosmetics.

Therefore, it is necessary to develop methods for evaluating and tracking exposure to nanoparticles of workers, consumers and the environment. Developing reliable aerosol sampling and analysing methods is thus a key issue in terms of public health and prevention of risks in a work station. In particular, developing sampling devices suitable to be portable and attached singly to a working suit of a worker at a station for making nano-objects or developing nanomaterials could turn out to be imperative.

The sampling or sampling processing method choice, that is currently favoured, consists in sucking an air flux likely to be particle-loaded through a filter which is ex post analysed by various techniques (gravimetry, microscopy, XRF, . . . )

From prior art, sampling devices, also called cassette samplers, are already known, which are portable and which have to sample an aerosol contamination likely to be inhaled by the mouth or nose of an individual when he breathes.

Thus, U.S. Pat. No. 4,961,916 relates to a device for sampling gases and particulate pollutants comprising a cassette inside which three filters are stacked upon each other and comprising two ports on either side of these filters, the first one opening into the outside environment likely to be polluted and the other on a pipe connected to a suction pump. Thus, from upstream to downstream, upon suction by the pump, the first filter enables to collect only the particulate fraction of the aerosol, the second, impregnated beforehand with a reactive, enables to selectively react with one or more gaseous compounds and the third filter has only the function of rigidifying the filtering assembly. The sampling aimed at in this patent is collecting gaseous and particulate isocyanates which are in polluted air.

U.S. Pat. No. 5,205,155 in turn discloses a device for sampling asbestos fibres likely to be suspended in air and concerns the non-uniform deposition on the filter accommodated in the sampling cassette. The patent proposes, to overcome this, to shape the cassette inlet, that is the one in proximity of the suction port of the environment concerned, as a flared shape and to make it smooth in order to promote a homogeneous particle deposition onto the filter.

US Patent Application 2008/0196514 A1 relates to a device for individually sampling dust which is used to collect the inhalable fraction of airborne particles.

This patent describes different aspect ratios of the cassette (length L/to inlet diameter D of the aperture ratios), which, according to it, enable suction sampling to be improved. Furthermore, this patent mentions that to have the best representativity of inspiration through nose, it is advantageous to provide a vertical orientation of the air flux sucked from bottom to top.

The aerosol sampling methods and devices of prior art have one or more major drawbacks which can be summarized as follows:

most aerosol sampling methods require to extract the filter from its cassette in situ. The implementation devices are thus provided to open the cassette readily and by any person: opening with an unintentional extraction can thus result in an outside contaminations of the filter, a loss of material adsorbed onto the filter or a poor traceability of the filter. In particular, an operator working in a station for making nano-objects or developing nanomaterials can unintentionally open a cassette, contaminate a filter, put an already used one, etc.

upon sampling, it is necessary to have the best representation of the particulate fraction inhaled by the mouth and nose of an individual. But, some methods described in the literature have an orientation of the sampling device which is not optimum, which can make the interpretation of results uncertain.

The general purpose of the invention is thus to provide a device for sampling and transporting nano-objects likely to be present in an aerosol for the elementary analysis thereof which does not have the aforementioned drawbacks, and which thus enables to ensure the sampling integrity and definitely providing the traceability thereof up to the actual analysis.

It is set out that the elementary analysis is an analysis allowing to determine what atomic elements (Titanium, Carbone, Nickel, etc.) are present as well as their atomic percentage in the sample. On the other hand, an elementary analysis does not enable the structure or assembly of these elements together to be determined.

A particular purpose of the invention is to provide a device of this type which is simply made and inexpensive.

DISCLOSURE OF THE INVENTION

To do this, the object of the invention is a device for sampling and transporting nano-objects likely to be present in an aerosol for the analysis thereof, comprising a porous sampling filter capable of trapping nano-objects likely to be suspended in the aerosol, a cassette consisting of a first part and a second part which are provided with mutual assembly means and filter holding means, the first and second parts defining, in their assembled position, a cavity wherein the filter is accommodated by being held, and at least one seal capable of sealing between the cavity and outside.

According to the invention, the mutual assembly means comprise:

first clipping means integral with the first part,
second clipping means integral with the second part and capable of cooperating with the first means for clipping both parts; the first and second clipping means being configured not to be accessible from outside in the assembled position of the parts.

Furthermore, one of the parts is provided with holes opening each at a time onto outside of the parts and on one of the cooperation zones of the clipping means, the holes being each capable of accommodating a pin for unclipping both parts by applying a thrust force on the pins against the first or second clipping means.

By the phrase "not being accessible from outside", it is meant that the clipping means can be physically reached only through pins individually accommodated in the holes but not manually or by using a tool from the space outside to the device in its assembled position.

Thus, by virtue of the clipping means, the cassette is secured which cannot be unintentionally opened, the opening thereof for the actual analysis of the sample requiring a tool suitable for separating both portions of the cassette.

This cassette is comprised of two parts between which is located a filter holder acting to support the filter by keeping it tensioned and planar and participating in the sealing between the upper and lower portions of the cassette. Finally, the cassette has in its median portion an opening enabling the identifier of the filter holder to be read.

According to the present invention, the three components of the cassette are characterised in that they are made of plastic material.

Furthermore, as explained herein below, it is provided according to the invention a simple and judicious filter identifying system which is accessible from outside of the cassette without having to open the same. This identifying system allows a perfect traceability of sampling until the analysis report is issued.

According to an advantageous embodiment, the first clipping means consist of a number equal to n of elastically deformable tabs which end is shaped as a hook and which are arranged on the first part by being relatively distant from each other at an angular position equal to $2\pi$ divided by the number n, that is $2\pi/n$, and the second clipping means consist of a same number n of recesses or lugs shaped by being complementary to the hooks and arranged on the second part by being relatively distant from each other at the same angular position at $2\pi/n$ as the tabs. Preferably, the number n is between 2 and 20, further preferably between 2 and 4.

The filter holder means advantageously comprise two shoulders, one made on an inner periphery of the first part and the other on an inner periphery of the second part, and the device comprises a filter holder pinchedly held between both shoulders.

The filter holder is preferably compressively deformable in order to be crushed by the first and second parts in the assembled position and thus to make up a single seal.

The device preferably comprises at least one elastomeric seal pressing against at least one of the shoulders.

As regards the material used, the first and second parts and the filter holder are advantageously based on thermoplastic material, preferably of polyethylene terephthalate (PET), polybutylene terephthalate (PBT), polymethylmethacrylate (PMMA), polyamide 6 (PA6), polyamide 66 (PA66), polycarbonate (PC), polypropylene (PP) or polyoxymethylene copolymer (POM-C). The material(s) forming the parts and/or the filter holder can contain a carbon black filler having an antielectrostatic function.

The mutual assembly means can further comprise an annular edge on each of the first and second parts in order to perform, in addition to clipping, mutual surface pressing between the parts in their assembled position.

As regards the attaching mode of the filter holder, it is advantageously provided that at least one of the parts comprises a notch opening on either side of the annular edge and in that the filter holder comprises a tongue complementary to the notch(es) and on which a filter identifying element is attached, such that in the assembled position of the parts, the identifying element is in contact with the outside environment.

By the phrase "in contact with the outside environment", it is meant that the identifying element comes up in the space outside to the device in its assembled position.

The identifying element is preferably an electronic chip or a radiofrequency identification (RFID) tag or a two dimensional bar code, of the Datamatrix® type. It can be attached by a bonding technique, through etching, overinjection or indirect gravure printing.

The invention also relates to a tool for performing unclipping of both parts of the device previously defined, comprising pins arranged relatively distant from each other at the same position as the holes.

The tool can further comprise mechanical guide means capable of guiding the tool relatively to the part provided with holes to facilitate the simultaneous pushing of the pins against the first or second clipping means.

The invention finally relates to the use of the device previously defined, as a device for tracking exposure of operators in a station for making nano-objects or developing nanomaterials.

BRIEF DESCRIPTION OF THE DRAWINGS

Further characteristics and advantages of the invention will better appear upon reading the detailed description of the invention, made by way of illustrating and not limitation in reference to the following figures wherein.

DETAILED DISCLOSURE OF PARTICULAR EMBODIMENTS

To be able to perform the sampling of nano-objects likely to be contained in an aerosol, the device according to the invention first comprises a filter 30 suitable for trapping nano-objects likely to be suspended in air, which is accommodated and held in a cavity formed by a cassette C in a closed configuration.

Thus, the sampling method according to the invention consists in orienting the closed cassette such that the air to be analysed is sucked by a pump not represented from a port 20 and comes out through the port 10 to go then to the pump.

The suction can of course be provided according to a reverse path, that is from the port 10 to the port 20. The nano-objects or micrometric size particles thus sucked will be collected on the filter 30 held in the cassette. It is provided in the sampling method according to the invention to orient the cassette such that the sampling is the most representative either of breathing though the mouth, or through the nose. Thus, preferably, to simulate breathing through the nose, the cassette is oriented such that it is vertical with the suction port 20 downwards and that there is a suction from bottom to top. Likewise, preferably, to simulate breathing through the mouth, the cassette is oriented to have the suction port 20 horizontally.

As represented, the device according to the invention enables the sample sampling and the transport of trapped nano-objects, in a secured way and with a perfect traceability.

To do this, the cassette consists of two parts 1, 2 of generally cylindrical shape.

The upper part 2 is provided with flexible tabs 21 or in other words elastically deformable, which end is shaped as a hook 210.

The lower part 1 is provided with recesses 11 individually complementary to a tab 21 with an end also recessed or as a bump complementary individually with a hook 210. It can of course be provided within the scope of the present invention with an arrangement of hooks or reversed complementary bump, that is with hooks individually in a recess of the part 1 and with tabs with a bump on the part 2.

The relative angular arrangement between the flexible tabs 21 of the upper part 2 is identical to that of the recesses 11 of the lower part 1.

Figure 1:
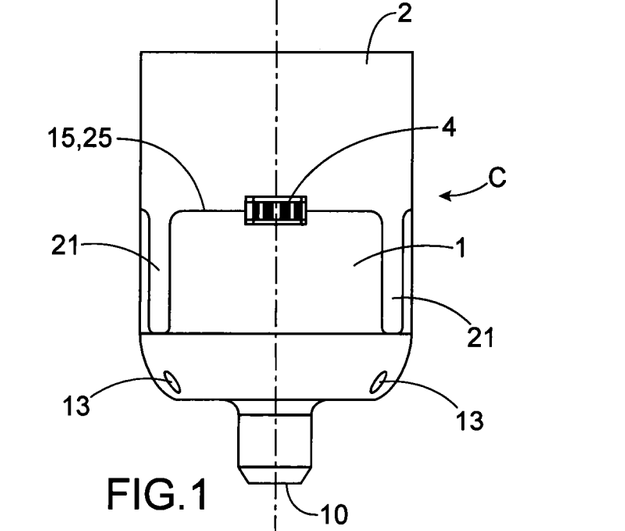
FIG. 1 is a profile view of the cassette for sampling a device according to the invention, the cassette being in a closed configuration.

Thus, in the mutual assembled position, the tabs 21, with their hooks 210 come to smugly fit and accurately clip in the recesses 11 and recesses or bumps 110 (FIG. 1). In this mutual assembled position, no tab 21 projects from the parts 1, 2: in other words, no clipping means 11, 110, 21, 210 is accessible from outside and only the use of an adequate tool 5 as described hereinafter enables both parts to be disunited. By virtue of the invention, any unintentional opening of the cassette outside of the analysis laboratory intended to accurately analyse the particles trapped by the filter 3 is prevented. Thus, the contamination risks thereof are restricted, which are not really representative of the sampling which could occur either by an increase in the amount of particles trapped by the filter, or by a decrease in the amount of particles trapped on the filter (peeling off) or by addition of particles having a nature different to those sampled.

The lower part 21 is provided with holes 13 opening both to outside and on the zone where the bumps or recesses 110 are arranged, that is at the zone where the tabs 21 with theirs hooks 210 cooperating by clipping on the corresponding bumps or recesses 210. Therefore, there are as many holes 13 as complementary clipping means.

For unclipping both parts 1, 2, in each hole is inserted a pin 50 having a sufficient length to reach the bump 110 or the hook 210 in the clipped position. Thus, a thrust force onto the pins 50 accommodated in the holes 13 comes to unhook the hooks 210 from their corresponding bumps, which disunites both parts 1, 2.

Figure 3:
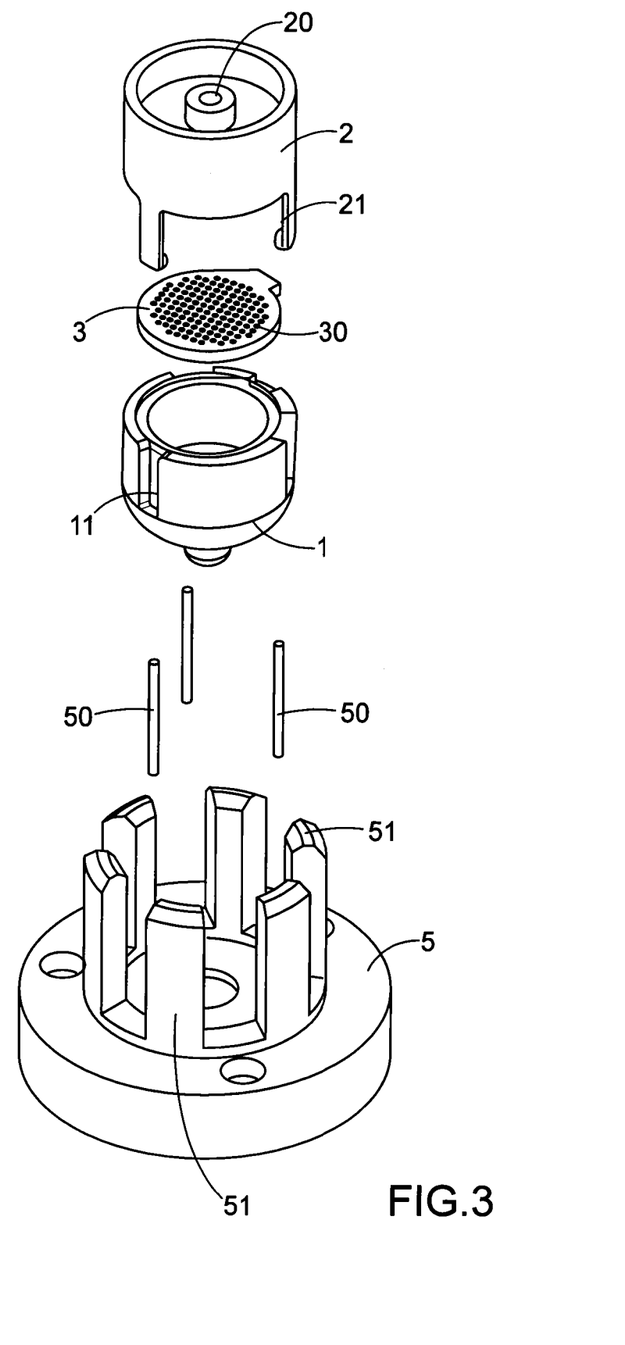
FIG. 3 is a view identical to FIG. 2 further showing a tool in accordance with the invention allowing the secured opening of the cassette.

Advantageously, all the pins 50 are attached on a tool 5 represented in FIG. 3 which also comprises rigid tabs 51 distant from each other so that they can accommodate the cylindrical body of the lower part 1. In other words, these rigid tabs 51 act as a guide to facilitate the simultaneous thrust of the pins 50 against the hooks 210.

Alternatively, the tabs can be located on the lower part and the holes on the upper part, without departing from the scope of the invention.

The filter 30 is in turn supported by a filter holder 3. In the assembled position of both parts, the filter holder 3 is held pinched between both shoulders 14, 24, each made on an inner periphery of one of both parts 1, 2.

Advantageously, the filter holder 3 is selected in an elastically deformable material and thus has the further function of a seal between the lower 1 and upper 2 parts of the cassette C. In other words, a filter holder 3 can be advantageously provided, with a hardness lower than the materials of the parts 1 and 2 of the cassette, in order to be crushed against the facing shoulders 14, 24, by pressing upon clipping.

Since the filter holder 3 has the function of being a mechanical support to the filter 30, it can have a generally annular shape or be made of a solid part through which a multitude of through holes passes via upright channels throughout the thickness of the part, this multitude of holes thus forming the filter itself. In any case, it is carefully controlled that it generates a minimum of pressure losses at the suction.

The filter can consist of alumina membranes; silica, quartz or borosilicate fibres; cellulose or derivatives thereof such as methylcellulose (MCE); polyvinylidene fluoride (PVDF); polyestersulfone (PES); polystyrene (PS); polytetrafluoroethylene (PTFE). Generally, it is a few micrometers to a few tens of micrometers thick, for example 10 to 200 micrometers. Typically, the pores of the filter have a unit size between 5 and 30 μm.

It can also be advantageously provided, in accordance with the invention, to provide the filter holder with a complementary tongue 31 with notches 12, 22 each made of one of both parts, such that in their assembled position, the end of the tongue 31 is in contact with the outside environment (FIG. 1). Thus, by making an identifying element 4 on the tongue 31, a simple and efficient traceability can be provided without having to open the cassette C. This possible traceability throughout the lifetime of the filter 30 enables, among other things, the association of the sampling of a given aerosol which occurs in the proximity of a particular workstation with an analysis report of the filter even if a few days elapse between sampling and the actual analysis. Any inopportune filter exchange can further be avoided, which could happen by handling by a worker in a station for making nano-objects or developing nanomaterials and would induce consequently a poor worker-sampled filter attribution. In other words, a poor tracking of the exposure of a given worker to his work station is avoided. This break in traceability would compromise tracking the exposure of workers to the nanomaterials.

Thus, as shown in FIG. 1, the identifying element 4 remains visible or accessible even when the cassette is closed due to both notches 12, 22. The identifying element 4 associated with the filter holder 3 can be made in different ways: it can be a tag with an alphanumeric code. It can also be a DataMatrix® type 2D code. It can also be a wired connection with a chip embedded in the filter holder 3. Thus, the identifying element 4 containing information relating to the filter 30 and its support 3 is integrated within the filter holder either by a so-called overinjection technique, or by an indirect gravure printing, bonding, or etching technique.

By the term overinjection, it is intended a technique which enables the identifying element 4 to be integrated within the tongue 31 of the filter holder 3 when manufactured. The identifying tag 4 is placed inside a moulding tooling between the fixed part and the movable part of the mould. Upon closing the mould, the tag 4 comes to press against the filter holder 3 through suction, without bonding or coating product. In this way, the tag 4 slap fits into the location provided in the mould and it cannot be ripped off the filter holder 3.

By the term bonding, it is meant any physical or chemical assembly process which enables via a glue or adhesive to assemble the material of an identifying element 4 and the filter holder 3.

By the term indirect gravure printing, it is meant any indirect printing process (ink transfer) which enables an identifying element 4 to be directly transferred onto the filter holder 3.

By the term etching, it is meant any process which enables the filter holder 3 to be dug (laser marking, micropercussion) and therefore an identifying element 4 to be created.

According to the invention, a placement of the identifying element 4 can be provided which comes from a combination of the previously mentioned techniques.

In order to have a device light and simple to implement, both parts of the cassette 1, 2 and the filter holder 3 can be made by thermoplastic material based injection, preferably of polyethylene terephthalate (PET), polybutylene terephthalate (PBT), polymethylmethacrylate (PMMA), polyamide 6 (PA6), polyamide 66 (PA66), polycarbonate (PC), polypropylene (PP) or polyoxymethylene copolymer (POM-C). The materials can possibly be filled (for example with glass fibres or carbon fibres) and additives can possibly be used to improve the intrinsic characteristics of the material selected. Among these additives, compounds giving antistatic properties can be contemplated. It can also be contemplated to make the parts 1, 2 and 3 through machining a block of thermoplastic material.

With thermoplastic materials, the device according to the invention can thus be made in such an inexpensive way as to make it disposable. It can also be contemplated to perform, once the sampling analysis is made, an appropriate washing of the cassette to use it again and thus perform a recycling of the parts 1, 2.

To further improve the mutual assembly of both parts 1 and 2, an annular edge 15, 25 can be provided on each of them in order to perform in addition to clipping, mutual surface pressing between the parts in their assembled position (FIG. 1).

Prior to any sampling, the cassette should have a filter suitably positioned therein. The latter thus includes the filter 30, lying on a support 3 which is held between the complementary parts 1 and 2. The cassette, once it is closed, allows the passage of a gas flux from the inlet port 20 to the pump connected to the outlet port 10 by passing through the filter 30. O-rings located on either side of the filter holder 3 ensure that the flux flow occurs through the filter and that there is no leak. Besides, flow rate measurements have been performed on an ad hoc basis respectively at the inlet port 20 and the outlet port 10: the values obtained are identical when the operating pump is connected to the cassette.

When the cassette is not connected to a pump, it is necessary to fill the ports 10 and 20 using adequate plugs in order to avoid accidental contaminations. On the other hand, when the latter is connected to a pump through the port 10, it is necessary to keep the port 20 open. The inventors have noticed that an optimum operation of this sampling cassette is achieved for air flow rates ranging from 0.1 to 5 L·min$^{-1}$. Advantageously, the flow rate used is between 1 and 2 L·min$^{-1}$.

It is evident that other improvements or alternatives can be made without departing from the scope of the invention.

Figure 2:
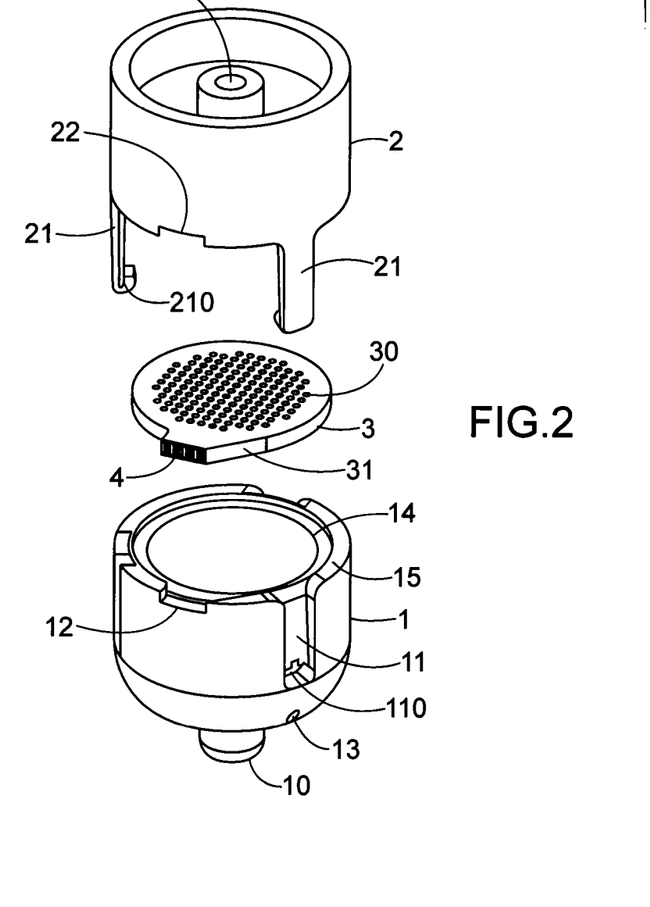
FIG. 2 is an exploded perspective view of the device according to FIG. 1 showing both parts of the cassette in non-assembled position and the filter with its filter holder.
Figure 4:
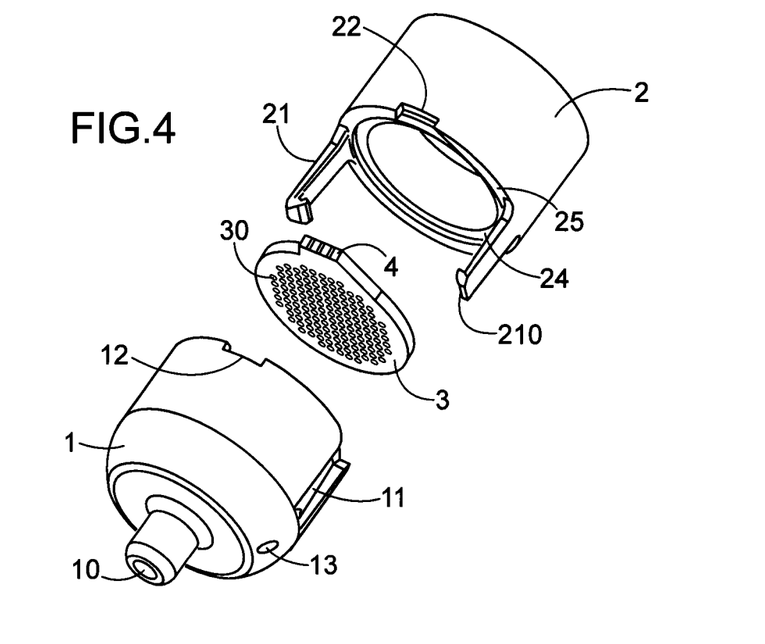
FIGS. 4 and 5 are exploded perspective views showing alternative embodiments of the device according to the invention.
Figure 5:
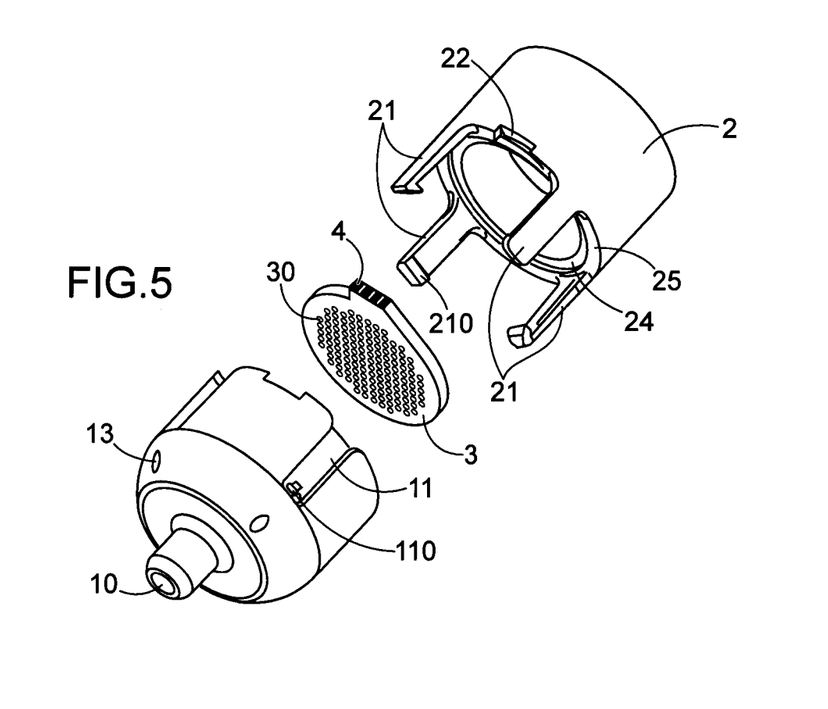

Thus, for example, in the alternative illustrated in FIGS. 1 to 3, the number of flexible tabs 21 with a hook 210 cooperating with the recesses 110 is equal to three, their relative angular positioning being 120° with respect to each other. FIG. 4 shows another alternative with two flexible tabs 21 at 180° to each other and FIG. 5 shows a further alternative at 90° to each other. More generally, the mechanical securing of the opening of the cassette can be achieved thanks to an number equal to n clipping means, of male type, integral with one of the parts 1, 2 and arranged at an angular position of $2\pi/n$ from each other and with the same number n of female type clipping means on the other part. Therefore, an unclipping tool 5 is defined with a corresponding number n of pins 50 to be able to disunite both parts 1, 2 of the cassette.

Likewise, if in the illustrated embodiments, the clipping means are integrally made with the parts 1, 2 of the cassette, an attachment can be provided through bonding, screwing or else, etc.

Besides, further seals can be provided, preferably two elastomeric seals transferred and bonded onto the parts 1 and 2 at their interface.

The invention claimed is:

1. A device for sampling and transporting nano-objects likely to be present in an aerosol for analysis thereof, comprising:
    a porous sampling filter configured to trap nano-objects likely to be suspended in the aerosol;
    a cassette including a first part and a second part including mutual assembly means and filter holding means, the first and second parts defining, in their assembled position, a cavity in which the filter is accommodated by being held, and at least one seal configured to seal between the cavity and outside; wherein
    the mutual assembly means comprises:
    first clipping means integral with the first part,
    second clipping means integral with the second part and configured to cooperate with the first clipping means to clip both parts, the first clipping means including flexible tabs and the second clipping means including recesses shaped complementary to the flexible tabs so that the flexible tabs fit within the recesses and none of the flexible tabs project out from the recesses, and
    wherein the second part includes holes extending from an outside of the second part to cooperation zones wherein the first clipping means cooperates with the second clipping means, the holes each configured to accommodate a pin for unclipping both parts by applying a thrust force on the pins against the first or second clipping means.

2. The device according to claim 1,
    wherein the first clipping means includes a number equal to n of the flexible tabs with ends shaped as a hook and arranged on the first part by being relatively distant from each other at an angular position equal to $2\pi$ divided by the number n, $2\pi/n$, and
    wherein the second clipping means includes a same number n of the recesses shaped by being complementary to the hooks and arranged on the second part by being relatively distant from each other at the angular position $2\pi/n$ same as the tabs.

3. The device according to claim, wherein the filter holding means comprises first and second shoulders, the first shoulder made on an inner periphery of the first part and the second shoulder on an inner periphery of the second part, and wherein the device comprises a filter holder pinchedly held between the first and second shoulders.

4. The device according to claim 3, wherein the filter holder is compressively deformable to be crushed by the first and second parts in the assembled position and thus making up a single seal.

5. The device according to claim 3, comprising at least one elastomeric seal pressing against at least one of the shoulders.

6. The device according to claim 3, wherein the first and second parts and the filter holder are based on thermoplastic material, or of polyethylene terephthalate (PET), polybutylene terephthalate (PBT), polymethylmethacrylate (PMMA), polyamide 6 (PA6), polyamide 66 (PA66), polycarbonate (PC), polypropylene (PP) or polyoxymethylene copolymer (POM-C).

7. The device according to claim 1, wherein the mutual assembly means further comprises an annular edge on each of the first and second parts to perform, in addition to clipping, mutual surface pressing between the parts in their assembled position.

8. The device according to claim 7, wherein at least one of the parts comprises a notch opening on either side of the annular edge, and the filter holder comprises a tongue complementary to the notch and on which a filter identifying element is attached, such that in the assembled position of the parts, the identifying element is in contact with an outside environment.

9. The device according to claim 8, wherein the identifying element is an electronic chip or a radiofrequency identification (RFID) tag or a two dimensional bar code.

10. The device according to claim 8, wherein the identifying element is attached by a bonding technique, through etching, overinjection, or tampography.

11. The device according to claim 1, wherein the first part and the second part each have a generally cylindrical shape and the flexible tabs fit within the recesses such that the flexible tabs are flush with the cylindrical shape of the second part.

12. The device according to claim 1, wherein the cassette includes an inlet port and an outlet port through which the aerosol passes, and the inlet port is positioned in the second part and the outlet port is positioned in the first part.

13. A tool for performing unclipping of both parts of the device according to claim 1, comprising pins arranged relatively distant from each other at a same position as the holes.

14. The tool according to claim 13, further comprising mechanical guide means capable of guiding the tool relatively to the part including the holes to facilitate simultaneous thrust of the pins against the first or second clipping means.

15. The tool according to claim 14, wherein the mechanical guide means includes tabs protruding from the tool such that the tabs are configured to receive the part including the holes to guide the pins into the holes.

16. A device for sampling and transporting nano-objects likely to be present in an aerosol for analysis thereof, comprising:
a porous sampling filter configured to trap nano-objects likely to be suspended in the aerosol;
a cassette including a first part and a second part including means for assembling the first part and the second part and means for holding the filter, the first and second parts defining, in their assembled position, a cavity in which the filter is accommodated by being held, and at least one seal configured to seal between the cavity and outside: wherein
the means for assembling comprises:
first clipping means integral with the second part,
second clipping means integral with the first part and the first clipping means fit within the second clipping means to assemble the first part and the second part without the first clipping means projecting out from the second clipping means, and
wherein the parts first part includes holes extending from an outside of the first part to cooperation zones wherein the first clipping means cooperates with the second clipping means, the holes each configured to accommodate a pin for unclipping both parts by applying a thrust force on the pins against the first or second clipping means.

17. The device according to claim 16, wherein the cassette includes an inlet port and an outlet port through which the aerosol passes.

18. The device according to claim 17, wherein the inlet port is positioned in the first part and the outlet port is positioned in the second part.

* * * * *

UNITED STATES PATENT AND TRADEMARK OFFICE
CERTIFICATE OF CORRECTION

PATENT NO. : 9,457,348 B2
APPLICATION NO. : 14/349249
DATED : October 4, 2016
INVENTOR(S) : Clavaguera et al.

It is certified that error appears in the above-identified patent and that said Letters Patent is hereby corrected as shown below:

In the Claims

Column 8, Line 62, Claim 3 after "claim" insert --1--.

Column 10, Line 30, Claim 16 after "the" delete "parts".

Signed and Sealed this
Thirtieth Day of January, 2018

Joseph Matal
*Performing the Functions and Duties of the
Under Secretary of Commerce for Intellectual Property and
Director of the United States Patent and Trademark Office*